(12) United States Patent
Gerke et al.

(10) Patent No.: US 6,652,560 B1
(45) Date of Patent: Nov. 25, 2003

(54) BONE ANCHOR

(75) Inventors: Peter Gerke, Radevormwald (DE); Dietmar Hein, Kiel (DE); Clive Reay-Young, Harrogate (GB); Nicholas Woods, Harrogate (GB)

(73) Assignee: ArthroCare Corporation, Sunnyvale, CA (US)

( * ) Notice: Subject to any disclaimer, the term of this patent is extended or adjusted under 35 U.S.C. 154(b) by 157 days.

(21) Appl. No.: 09/608,139

(22) Filed: Jun. 30, 2000

(30) Foreign Application Priority Data

Jul. 3, 1999 (GB) .............................. 9915550

(51) Int. Cl.⁷ .............................................. A61B 17/04
(52) U.S. Cl. ....................................................... 606/232
(58) Field of Search ................................. 606/232, 233, 606/72, 74, 75; 623/13.13, 13.14

(56) References Cited

U.S. PATENT DOCUMENTS

| | | | |
|---|---|---|---|
| 5,176,682 A | | 1/1993 | Chow |
| 5,423,860 A | * | 6/1995 | Lizardi et al. .............. 606/232 |
| 5,472,452 A | * | 12/1995 | Trott ........................... 24/297 |
| 5,632,748 A | | 5/1997 | Beck, Jr. et al. |
| 5,647,874 A | | 7/1997 | Hayhurst |
| 5,707,395 A | | 1/1998 | Li |
| 5,797,963 A | * | 8/1998 | McDevitt ..................... 606/232 |
| 6,146,406 A | * | 11/2000 | Shluzas et al. .............. 606/232 |

FOREIGN PATENT DOCUMENTS

| | | |
|---|---|---|
| EP | 0 317 406 | 5/1989 |
| EP | 2 725 615 | 4/1996 |
| WO | 99/52472 | 10/1999 |

* cited by examiner

Primary Examiner—Michael J. Milano
Assistant Examiner—D. Jacob Davis
(74) Attorney, Agent, or Firm—John T. Raffle; Richard Batt

(57) ABSTRACT

The invention describes a bone anchor 76 comprising a head region 94 and supporting legs 78 and a method for soft tissue-bone grafting using the said bone anchor 76. A hole 84 is drilled through cortical bone 82 forming a socket 70 in a cancellous bone 90, and the bone anchor 76 is inserted therein thereby trapping ligaments 88*a* and 88*b* between the radially outermost portion of the anchor 76 and the inside surface of the socket 70. An optional expansion peg (not shown) is inserted into a hole 86 within the bone anchor 76, thereby causing the proximal ends of the legs 70 of the bone anchor 76 to expand radially causing the ligaments 88*a* and 88*b* to closely abut the cancellous bone 90 thereby encouraging the grafting process.

21 Claims, 4 Drawing Sheets

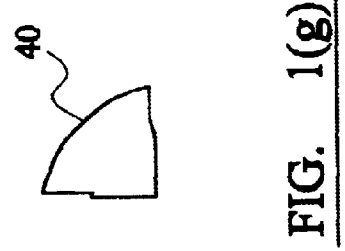
FIG. 1(g)
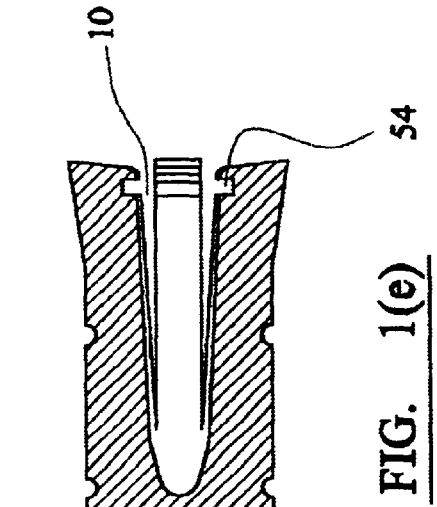
FIG. 1(e)
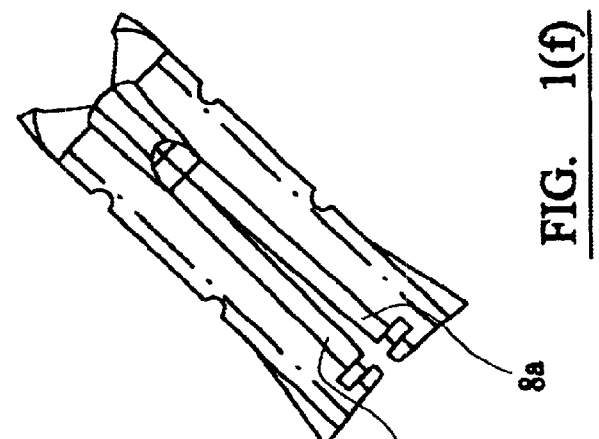
FIG. 1(f)
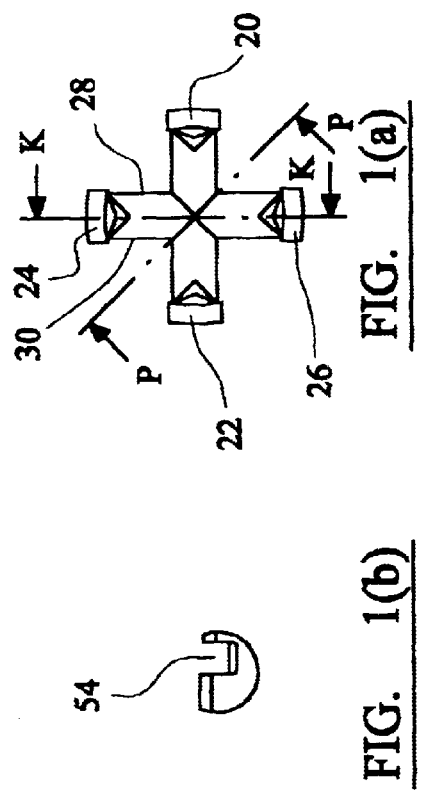
FIG. 1(a)
FIG. 1(b)
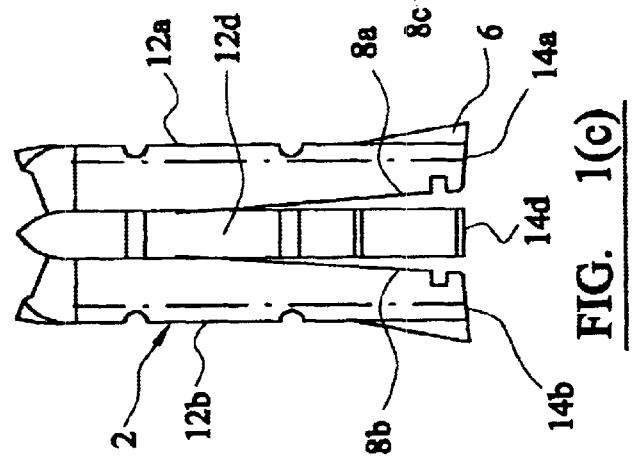
FIG. 1(c)
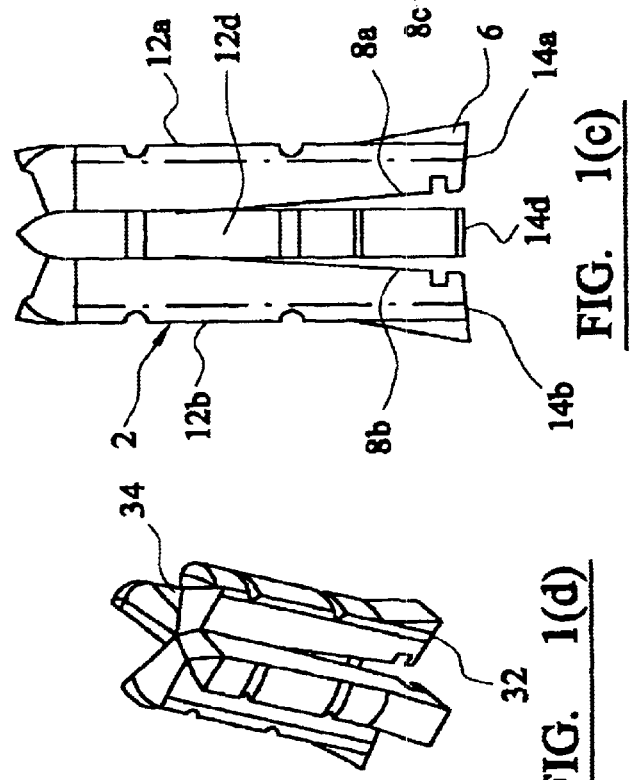
FIG. 1(d)

BONE ANCHOR

The present invention relates to a bone anchor, in particular, but not exclusively, to a bone anchor for graft fixation such as tendon or ligament fixation.

BACKGROUND OF THE INVENTION

Due to increasing involvement of people with active sport, injuries are becoming increasingly common where tissues such as ligaments or tendons tear or detach from bone. Surgical techniques have been developed to reconstruct such torn soft tissues and to re-attach them to the relevant bone. One of the most common types of such injuries is tearing of the Anterior Cruciate Ligament (ACL). The Anterior Cruciate Ligament connects the femur to the tibia at the centre of the knee joint. Reconstruction of such tissues generally involves replacement with a graft such as autologous or artificial tendon. An autologous tendon graft may be taken from the patients patellar tendon or, alternatively, the semitendinosus may be utilised. A typical fixation technique involves the use of a circular button fixation device which is located on the outside of the femur above the knee. As this is some distance from the site where the graft will be utilised in the knee joint, sutures are used to attach the graft to the femur button. The main disadvantage of this technique is that incisions need to be made through the skin and quadriceps muscle resulting in trauma to the leg and a cosmetically undesirable procedure. U.S. Pat. No. 5,645,588 describes an improved technique whereby the ligament anchor may be threaded through a femoral tunnel formed through the femur from the centre of the knee but such still involves the use of sutures attached directly to the fixation device on the outside of the femur above the knee and through which the graft is looped before passing out of the femoral tunnel before being secured to the tibia. Using such techniques inevitably involves the introduction of potential sources of loosening of the graft by way of stretching of the suture. This can cause movement in the graft during subsequent patient mobility which hinders the healing and grafting process. Furthermore, the use of sutures involves the tying of knots which themselves result in some subsequent stretch in the suture, increasing the likelihood that the graft will have inappropriate tension for its intended purpose. The suture itself may also fail under the high tensile forces to which it is subjected during use. PCT/US97/22061 attempts to solve this problem by providing an interference fit insertion element with a proximal apperture through which a graft may be threaded or attached. The technique involves securement of the interference end of the device into the central cancellous area of the bone. Unfortunately, this softer area of the bone may not provide sufficient anchoring of the device to resist the tensions to which the graft is subject in use.

U.S. Pat. No. 5037422 also relates to the anchoring of sutures for securement of a suture to a bore hole in a bone. The device is shown secured to the cancellous bone. The device is for use in soft tissue fixation to the outside of the bone and not fixation within the bore hole itself.

Futhermore, it is not suitable for graft fixation and is only applicable to sutures.

A device for graft fixation using sutures is described in EP 0 619 982 where the anchor includes a body and a plurality of barbs located in axially aligned, circumferentially spaced relation to each other about the body. The barbs have a normal configuration wherein they extend rearwardly and radially outwardly from the anchor body to outer ends which are normally located outside a longitudinal projection of the largest geometric cross-section of the body transverse to its longitudinal axis. The device utilises sutures and suffers from the drawbacks previously outlined. It also relies upon interference between the barbs and the soft cancellous bone area.

SUMMARY OF THE INVENTION

According to the present invention there is provided a bone anchor suitable for soft tissue-bone fixation comprising an anchoring member, the anchoring member having a head portion at the distal end thereof and supporting means at the proximal end thereof operable to be urged against the inside surface of the cortical bone, wherein soft tissue locating means are located on the exterior of at least the said head portion.

Advantageously, by having soft tissue locating means on the exterior of the head portion, the soft tissue may be securely located over the exterior of the head to anchor the soft tissue in position. Compression force may then be applied from the trailing ends of the soft tissue urging the support means against the inside surface of the cortical bone through which the hole has been drilled.

A further advantage of the locating means is that it allows the soft tissue to be anchored directly by the anchoring member without the need for interconnecting sutures.

To carry out its function of being urged against the inside surface of the cortical bone in the region around the hole that has been drilled, in use, at least a part of the supporting means is preferably wider or capable of being made wider than the hole that has been drilled.

Preferably, access means are provided in the body of the anchoring member to allow the soft tissue access from the exterior of the member to the hole in the bone.

The access means may be in the form of one or more apertures but, preferably, the supporting means is in the form of a number of legs depending from the head portion and a guide means or spacing between adjacent legs provides access from the exterior of the anchoring member to the hole in the bone.

Preferably, the locating means extends, at least partially, down the outside of the sides of the anchoring member to guide the elongate soft tissue and, preferably, urge it against the walls of the bone hole. Advantageously, this encourages grafting of the soft tissue to the surrounding bone.

Preferably, at least the lowermost portion of the supporting means at the proximal end of the anchoring member extends outwardly to a greater extent than the head portion.

The supporting means may be inwardly radially resiliently deformable at least at the said lowermost portion thereof, so that by compressing the sides of the supporting means radially inwardly, a lowermost portion which is wider than the bone hole may be eased therethrough and, upon release of the compression, the supporting means may then expand inside the hole so that the supporting means may then be urged back against the bone so that the bottom surface at proximal end of the supporting means abuts against the inside surface of the cortical bone in the region around the hole.

The legs may be thickened on the outside thereof at the proximal end to provide the wider lowermost portion of the anchor. Preferably, the anchor member is hollow and the thickness of the bottom surface at the proximal end thereof is such that, in use, the outermost portion of the surface is urged against the inside surface of the cortical bone around the region of the hole whereas the innermost portion of the surface projects over the hole. In this manner, when the proximal end comprises the ends of a number of legs, the gaps between adjacent legs provide access to the hole for tissue guided between adjacent legs. Alternatively, or in addition, the supporting means may be outwardly expandable, preferably, by use of expansion means.

Preferably, the supporting means may be expanded by means of a wedge means or an expansion tool Preferably, the supporting means comprise a number of legs depending from the head portion and the expansion tool or wedge means may be located between the legs to urge the legs radially outwardly with respect to the bone hole. The wedge means may be driven into the anchor means to urge the legs radially outward with respect to the hole. The wedge means may be left in the anchor after use. The wedge means may be in the form of a peg but any suitable shape which could be accommodated by the anchor between the legs may be employed.

Preferably, at least three legs depend from the head portion, more preferably, at least four legs, most preferably, four legs depend from the head portion. The legs may merge together above the lowermost portion and be spaced apart only at the proximal end of the anchoring member.

Preferably, the wedge means is narrower than the hole drilled so that, in use, access to the hole is possible radially outward of the wedge means.

Preferably, the locating means comprises a recessed portion over the distal end of the anchoring member which is suitable to securely locate elongate soft tissue such as tendon, ligament or substitutes therefor. Preferably, the locating means comprises a guide means across the distal end for the elongate soft tissue. Preferably, the recessed portion forms a guide portion for the said elongate soft-tissue. Preferably, there are two such guide means or portions which, preferably, cross each other at the centre of the outside of the said head portion. Preferably, the said two guide portions are substantially at right angles.

The head portion may comprise the distal ends of the legs where the latter merge together at the said distal ends thereof.

Typically, a guide channel is at least partially formed between adjacent legs. At the proximal end, where the legs separate, the channel may be formed by the adjacent sides of neighbouring legs and the wedge means between the said legs.

The head portion may be formed by the merging of the said legs. Preferably, by the merging of at least three such legs, more preferably by the merging of at least four such legs, most preferably, by the merging of four such legs. Preferably, the legs are equidistant.

The recessed portion may be formed by the top surface of the legs, at the distal end thereof. Preferably the top surface of each leg is angled downwardly toward the centre of the head portion to thereby provide the said recessed portion which prevents elongate soft tissue located over the head from sliding off the head in use.

Preferably, the wedge means may be secured in the anchoring member by suitable means to prevent it coming out in use. In some embodiments, the wedge means and inside surface of the legs co-operate in a rib and groove arrangement. The groove may be located on the legs or on the wedge means but to ease entry of the wedge between the legs, the rib is generally located around the wedge means at the proximal end thereof and corresponding grooves are found on the inside of the legs at the proximal end thereof Preferably, elongate guides extend down the outside of the bone anchor to guide elongate soft tissue, preferably, the guides are recessed into the sides of the bone anchor.

Preferably, the area between the sides of adjacent legs forms an elongate guide to guide the elongate soft tissue from the head portion to the bone hole.

Preferably, the guide is designed to only partially accommodate the full thickness of the elongate soft tissue, so that, in use, the latter is urged against the walls of the hole to encourage grafting thereof.

Preferably, the anchoring member is designed so that a compression force applied at the head portion causes the legs to splay outwardly. Preferably, the bottom surface of the proximal end of the anchoring member legs are distally angled toward the centre line of the anchoring member so that outward splaying of the said legs causes the angle to diminish until the said bottom surface lies substantially in the same plane as the cortical bone against which it abuts. Advantageously, in use, this causes the part of the proximal end in contact with bone to lie flat against the inside surface of the bone for added strength and security. Preferably, in use, the radially outermost part of the bottom surface abuts the region of the inside surface of the cortical bone around the hole and the innermost part extends over the hole in the bone to provide with the adjacent leg an exit hole for the elongate soft tissue and to urge the soft tissue against the cortical bone of the hole to facilitate grafting.

Examples of elongate soft tissue for use with the invention include ligament or tendon, in particular, reconstructed ligament or tendon.

The invention extends to a method of soft tissue-bone fixation utilising the bone anchor. In particular, ligament or tendon fixation at a suitable joint such as the knee, elbow or shoulder. The invention is particularly advantageous in reconstruction of the Anterior Cruciate Ligament (ACL) in the knee or the posterior cruciate ligament (PCL) in the knee. In particular, femoral fixation of the reconstructed ligament. Especially, fixation at the intercondylar notch by mounting the bone anchor on the interior surface of the cortical bone at the intercondylar notch.

According to a second aspect of the present invention there is provided a method of anchoring a graft in a bone comprising the steps of:

forming a tunnel or opening in the bone to a predetermined depth;

securing the graft to the bone anchor so that the trailing ends of the graft extend below the proximal end of the anchor;

inserting the anchor and graft in the tunnel or opening;

and pulling the graft trailing ends to urge the proximal surface of the anchor into contact with the inside surface of the cortical bone around the region of the hole.

Preferably, by pulling the trailing ends, the graft is urged into contact with the walls of the hole.

According to a further aspect there is provided a method of anchoring a bone anchor comprising the steps of:

forming a tunnel or opening in the bone to a predetermined depth;

securing soft-tissue to the anchor;

mounting the bone anchor on the inside surface of the cortical bone;

employing compression means to urge the bone anchor against the said inside surface to provide soft-tissue anchoring.

Preferably, the soft-tissue is elongate and is secured to the anchor so that its trailing ends extend below the proximal end of the anchor.

Preferably, the compression is applied by tensioning the said soft-tissue trailing ends.

Preferably, the soft-tissue is a ligament or tendon graft, more preferably, an ACL or PCL graft.

Preferably, the bone anchor is mounted on the inside surface of the cortical bone at the intercondylar femoral notch, preferably, on the inside surface or distal surface of the cortical bone immediately adjacent the wall of the hole drilled therethrough. The bone anchor may have a plurality of simultaneous mounting points, preferably, at least two, more preferably at least three, most preferably, at least four. Preferably, the mounting points are equally circumferentially spaced with respect to the round hole. Preferably, the mounting points are provided by proximal mounting surfaces at the ends of legs of the bone anchor.

Preferably, the graft is secured to the bone anchor by locating the graft over the outside of a bone anchor according to the first aspect of the invention by placing the graft thereover via the locating means.

Preferably, the method includes the step of locating the graft along the sides of the anchor, preferably, by passing it down elongate guide means located on the side thereof.

Preferably, the method includes the step of expanding the walls of the anchor in the tunnel using wedge means or an expansion tool. Preferably, the wedge is urged up the hollow centre of the anchor to urge the sides outwardly into contact with the walls of the hole and to preferably, provide sufficient contact between the proximal surface of the anchor and the inside surface of the cortical bone so that the anchor is mounted on the said inside surface of the cortical bone.

Preferably, the method includes locating at least two elongate grafts in this manner, preferably, substantially at right angles to each other.

Preferably, the bone anchor comprises bio-compatible materials. For instance, the material may be bio-absorbable material or a non-absorbable permanent material. Such absorbable materials may include trimethylene carbonate copolymers, polylactic acid and polyglycolic acid. Examples of non-absorbable materials include polyethylene, polypropylene, polyester and acetal homopolymers. Alternatively, copolymers of any of the foregoing may be utilised.

BRIEF DESCRIPTION OF THE DRAWINGS

An embodiment of the invention will now be described by way of example, with reference to the accompanying drawings in which:

FIG. 1a is a plan view of a bone anchor in accordance with the first invention;

FIG. 1b is a detail of a peg securing groove in accordance with the present invention;

FIG. 1c is a front elevation of the bone anchor of FIG. 1a;

FIG. 1d is a perspective view of the bone anchor;

FIG. 1e is a cross section along a line K—K of figure 1a;

FIG. 1f is a cross section along line P—P of FIG. 1a;

FIG. 1g shows a possible tendon profile of a tendon located over the bone anchor;

FIG. 2b is a detailed view of part of the rib at the proximal end of the peg of FIG. 2a.

DETAILED DESCRIPTION OF PREFERRED EMBODIMENTS

Figure 2A:
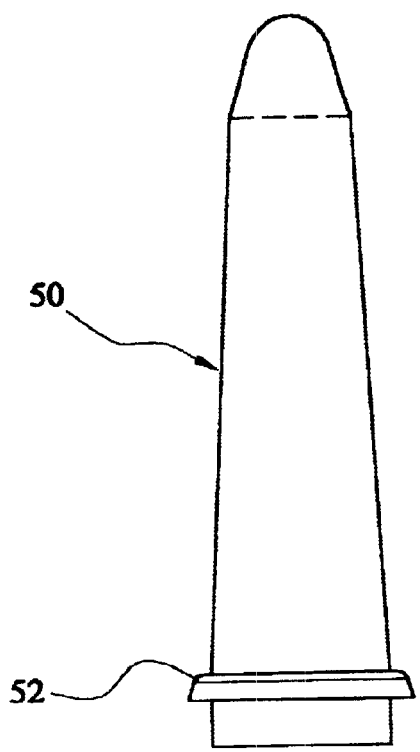
FIG. 2a is a peg according to the present invention.
Figure 2B:
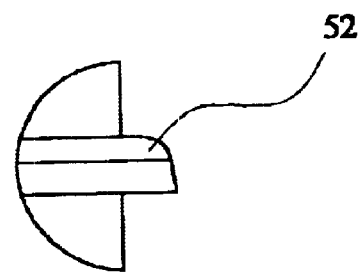

Referring to FIGS. 1 and 2, a bone anchor 2 comprises four elongate coextensive legs which are arranged in cruciform in plan view. Each leg has a generally non uniform rectilinear section. The legs are merged together at the upper distal end 4 of the bone anchor but separate as they extend to the proximal end 6 of the bone anchor.

After separating the inside faces 8(a–d) of the legs radiates outwardly as it extends towards the proximal end 6 so that a wedge receiving socket 10 is formed by the space between the legs on the inside of the bone anchor 2. The exterior surfaces 12(a–d) of each leg are arcuate in section to closely accommodate the bore hole profile. The main part of this surface of the leg extends parallel with the corresponding surface on the opposed leg. However, the surface extends radially outwardly at the proximal end 6 of the bone anchor 2 to form a thickened radially outermost portion 32 of each leg and extends radially inwardly at the distal end 4 of the bone anchor 2. The lower surface 14(a–d) of each leg at the proximal end 6 thereof is angled distally towards the centre line of the bone anchor so that a flat surface is presented to an underlying bone surface when the legs 20–26 splay outwardly under compression forces acting at the distal end 4 of the bone anchor 2. The compression force is provided by elongate grafts which are located over the distal end 4 and guided between adjacent legs of the bone anchor. At the distal end 4 of each leg 20–26, the leg upper end surface angles proximally towards the centre of the bone anchor. In this manner, a recess is provided at the distal end 4 of the bone anchor.

The sides 28, 30 of each leg extend parallel with each ocher and are generally planar along the whole of their length. However, the sides are thickened at the proximal end 6 of the bone anchor by the outwardly thickened portion 32 which also extends circumferentially at the lateral edges thereof. At the distal end of the legs, the sides angle inwardly to meet each other in an apex 34. The line of the apex itself is angled proximally towards the centre of the bone anchor as previously described.

Due to the shape of the bone anchor described, two reconstructed ligaments or tendons may be located cross wise over the distal end 4 of the bone anchor 2 so that the trailing ends thereof are guided down towards the bone outlet between adjacent legs. In this way, the reconstructed ligament or tendon is securely held in position between adjacent legs on opposed sides of the bone anchor and in the recess across the head of the bone anchor. The other reconstructed ligament or tendon is similarly located at right angles to the first reconstructed ligament or tendon. The trailing ends of the reconstructed ligaments or tendons may then pass out through the bone hole at the proximal end of the legs. By putting the trailing ends of the ligaments so fixated under tension, a compression force is applied to the bone anchor at the distal end thereof. This causes the legs 20–26 to splay outwardly to urge the legs into firmer engagement with the bore hole. As the proximal end of the legs is thickened, a proportion of the bottom surface 14 thereof is urged against the inside surface of the cortical bone through which the hole has been drilled. The splaying of the legs also causes the distally angled bottom surface 14 to come into the plane of the inside surface of the cortical bone providing a flat base for anchoring against the bone.

By locating the reconstructed graft on the outside of the bone anchor, the graft is encouraged to graft onto the walls of the bore hole and the cortical bone at the entrance to the tunnel. Furthermore, by increasing tension in the graft, which may occur during subsequent use by the patient, the bone anchor is urged outwardly with respect to the bore hole and the inside surface of the cortical bone causing more pronounced fixation.

Referring to FIG. 1g, the tendon profile located between adjacent legs 20, 26 is shown to follow the profile of the bore hole. By carefully constructing the replacement graft and/or the dimensions of the bone anchor, the tendon profile 40 may be urged radially outwardly into the bore hole and cortical bone at the outlet causing a greater likelihood of graft fixation. FIG. 2a shows a peg 50 which is designed to be close fitting with the peg receiving cavity 10 formed between the inside surfaces of the legs 20–26. In use, after bone anchor and ligament fixation, the peg may be urged into the peg receiving cavity 10. A circumferencial rib 52 is formed near the base of the peg 50 and a corresponding close fitting groove 54 is formed at corresponding heights on the inside surface of each leg 20–26. As the peg is urged further up the peg receiving cavity 10 the rib 52 eventually slots into the grooves 54 formed on the inside of each leg so that the peg will not-subsequently become dislodged. The peg provides two advantages in that it prevents the legs collapsing inwardly and also may force the legs outwardly to the radial extent to which they were designed.

Figure 3:
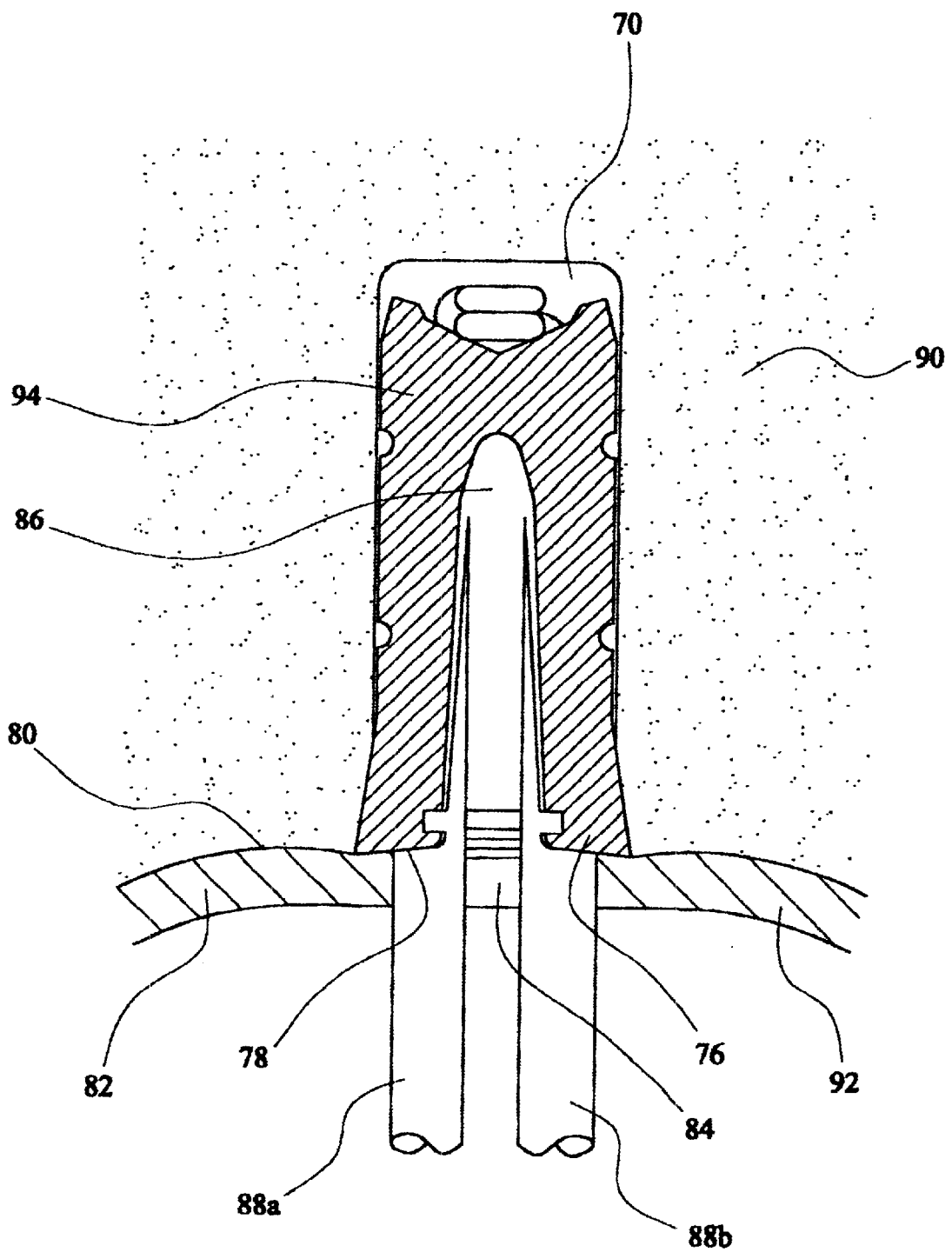
FIG. 3 is a cross-section through a bone anchor mounted on the inside surface of the cortical bone.
Figure 4:
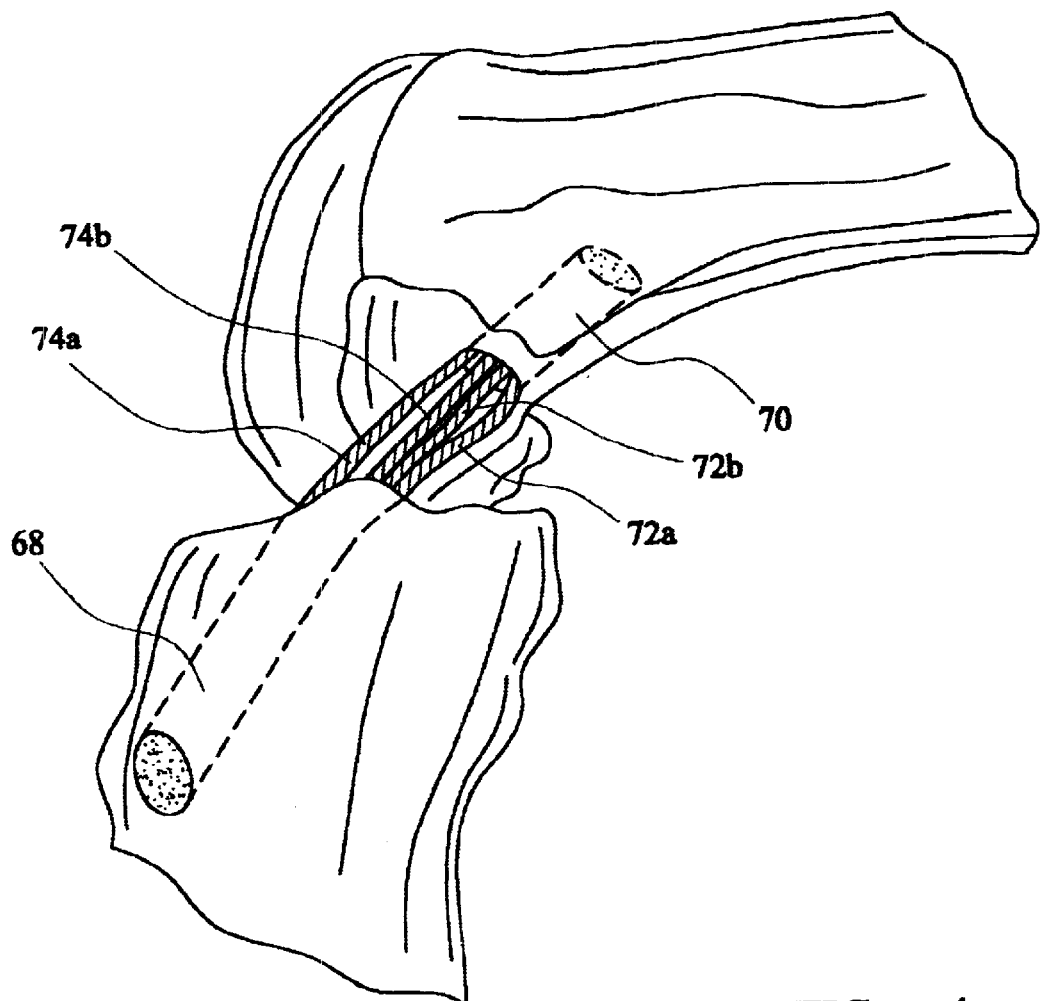
FIG. 4 shows a graft reconstruction of an ACL.

Referring to FIGS. 3 and 4, a bone anchor 60 of the type previously described with respect to FIGS. 1 and 2 is shown in cross section with reconstructed anterior crucimate ligaments 88 in position. One method of attaching a graft is that used in reconstructing the Anterior Cruciate Ligament (ACL) or the Posterior Cruciate Ligament (PCL). Initially, notchplasty is carried out at the intercondylar notch. This technique is described in U.S. Pat. No. 5139520 (Rosenberg), which is incorporated herein by reference, and is known to those skilled in the art. Typically, a drill guide is used to form a tibial channel 68. The isometric position required at the femoral surface is located using conventional surgical techniques and a closed end socket 70 is formed in the femur extending from the intercondylar notch at the angle required for ACL fixation. The length of the socket is relatively short and of the order of 2–3 cm. A pair of reconstructed ligaments are then located over the bone anchor as previously described. The bone anchor with the ligaments in position is then inserted into the intercondylar socket 70 as depicted in FIG. 3. Conventional techniques may then be carried out to secure the trailing ends 72, 74 at the tibia.

Referring to FIG. 3, the bone anchor 76 is of the same construction as that previously described with respect to FIGS. 1 and 2. The proximal surfaces 78 of the bone anchor 76 abut at the radially outermost portion of the surface against the inside surface 80 of the cortical bone 82 through which hole 84 has been drilled. The radially innermost portion of the surface of the proximal end 78 extends over the hole 84. The bone anchor 76 is shown prior to insertion of the expansion peg (not shown) which is to be fully inserted in an expansion peg socket 86 formed between the inside surfaces of the legs under the head portion 94. The effect of the insertion of the expansion peg is to cause the proximal ends 78 of the bone anchor 76 to expand radially and increase the proportion of the proximal end surface 78 which abuts against the s inside surface 80 of the cortical bone 82. Furthermore, during the surgical operation, the reconstructed ACL ligament 88 is tensioned to the required level which causes the legs to radially expand and thus further secures the bone anchor 76 in position. As is most clearly seen in FIG. 3, the effect of channelling the reconstructed ligament 88 around the outside surface of the bone anchor 76 causes the ligament to come into direct contact with the cancellous bone 90 and cortical bone 92 encouraging the grafting process. Furthermore, due to the absence of sutures securing the reconstructed ligament 88 to the bone anchor 76, there is a reduced risk of longitudinal movement of the reconstructed ligament 88 during use further increasing the likelihood that the graft will take. As a further advantage, the absence of sutures also prevent failure of the ligament anchor during use.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment (s). The invention extend to any novel one, or any novel combination, of the features disclosed in this specification (including any accompanying claims, abstract and drawings), or to any novel one, or any novel combination, of the steps of any method or process so disclosed.

What is claimed is:

1. A bone anchor suitable for soft tissue bone fixation comprising an anchoring member having a body and sides, the anchoring member having a head portion at a distal end thereof, supporting means at a proximal end of said anchoring member operable to be urged against an inside surface of the cortical bone, said supporting means being in the form of at least three legs depending from said head portion, and soft tissue locating means located-on an exterior of said head portion and extending, at least partially, down the outside of the sides of the anchoring member to guide elongate soft tissue.

2. A bone anchor according to claim 1, wherein at least a part of the supporting means is wider or capable of being made wider than a hole that has been drilled.

3. A bone anchor according to claim 1, wherein access means are provided in the body of the anchoring member to allow the soft tissue access from an exterior of the member to a hole in the bone.

4. A bone anchor according to claim 1, wherein a guide means or spacing between adjacent legs provides access from an exterior of the anchoring member to a hole in the bone.

5. A bone anchor according to claim 1, wherein the locating means is designed to urge, in use, the elongate soft tissue against walls of a bone hole.

6. A bone anchor according to claim 1, wherein at least a lowermost portion of the supporting means at the proximal end of the anchoring member extends outwardly to a greater extent than the head portion.

7. A bone anchor according to claim 1, wherein the supporting means is inwardly radially resiliently deformable at least at a lowermost portion thereof.

8. A bone anchor according to claim 1, wherein the legs are thickened on an outside thereof at a proximal end to provide a wider lowermost portion of the anchor.

9. A bone anchor according to claim 1, wherein the anchor member is hollow.

10. A bone anchor according to claim 9, wherein the supporting means is expandable by means of a wedge means or an expansion tool.

11. A bone anchor according to claim 10, wherein the expansion tool or wedge means is locatable between the legs to urge the legs radially outwardly with respect to a bone hole.

12. A bone anchor according to claim 1, wherein the supporting means is outwardly expandable.

13. A bone anchor according to claim 1, wherein the locating means comprises a guide means across a distal end for elongate soft tissue.

14. A bone anchor according to claim 13, wherein two guide means or portions are provided which cross each other centrally of an outside of said head portion.

15. A bone anchor according to claim 14, wherein said two guide portions are at such an angle to each other as to separate, in use, respective elongate soft tissue in each extending from the cross-over point.

16. A bone anchor according to claim 1, wherein a guide channel is at least partially formed between adjacent legs.

17. A bone anchor according to claim 1, wherein a distal surface of each leg is angled proximally towards a center of the head portion to thereby form said guide portion which prevents elongate soft tissue located over the head from sliding off the head in use.

18. A bone anchor according to claim 1, wherein elongate guides extend down an outside of the bone anchor to guide elongate soft tissue therein.

19. A bone anchor according to claim 18, wherein the guides are recessed into sides of the bone anchor.

20. A bone anchor according to claim 19, wherein the guides are designed to partially accommodate a full thickness of an elongate soft tissue.

21. A bone anchor according to claim 1, wherein the anchoring member is designed so that a compression force applied at the head portion in a proximal direction causes the legs to splay outwardly.

* * * * *